United States Patent
Lenfers (10) Patent No.: US 11,364,429 B2
(45) Date of Patent: Jun. 21, 2022

(54) TENNIS WALL

(71) Applicant: Alexander Lenfers, Vreden (DE)

(72) Inventor: Alexander Lenfers, Vreden (DE)

( * ) Notice: Subject to any disclaimer, the term of this patent is extended or adjusted under 35 U.S.C. 154(b) by 0 days.

(21) Appl. No.: 16/962,981

(22) PCT Filed: Jan. 11, 2019

(86) PCT No.: PCT/EP2019/025013
§ 371 (c)(1),
(2) Date: Jul. 17, 2020

(87) PCT Pub. No.: WO2019/141509
PCT Pub. Date: Jul. 25, 2019

(65) Prior Publication Data
US 2021/0113907 A1    Apr. 22, 2021

(30) Foreign Application Priority Data

Jan. 18, 2018 (DE) .......................... 102018000367.2

(51) Int. Cl.
| A63B 69/38 | (2006.01) |
| G09B 19/00 | (2006.01) |
| A63B 102/02 | (2015.01) |

(52) U.S. Cl.
CPC .......... *A63B 69/38* (2013.01); *G09B 19/0038* (2013.01); *A63B 2102/02* (2015.10); *A63B 2209/00* (2013.01)

(58) Field of Classification Search
CPC ............................... A63B 71/02; A63B 69/38
See application file for complete search history.

(56) References Cited

U.S. PATENT DOCUMENTS 1,566,945 A * 12/1925 Winkley ................. A63B 63/00
  473/173
1,658,097 A *  2/1928 Pierce ................. A63B 69/0097
  473/434

(Continued)

FOREIGN PATENT DOCUMENTS

| CN | 203196256 U | 9/2013 |
| CN | 205412155 U | 8/2016 |

(Continued)

OTHER PUBLICATIONS

Written Opinion of the International Searching Authority; European Patent Office; International Application No. PCT/EP2019/025013; dated Mar. 15, 2019; 7 pages.

(Continued)

*Primary Examiner* — Eugene L Kim
*Assistant Examiner* — Christopher Glenn
(74) *Attorney, Agent, or Firm* — Taft Stettinius & Hollister LLP (57) ABSTRACT

The present invention relates to a tennis wall (100), comprising a frame that can be erected on the ground (101) and a cloth (102) stretched in said frame (101), wherein the cloth (102) is stretched such that a level cloth surface (104) is formed and that a tennis ball hitting the cloth surface (104) rolls or slides up the cloth surface (104) and then rolls or slides down again, characterized in that a recess (105) is provided on the upper end (103) of the cloth (102), the recess (105) being designed and positioned such that a tennis ball, once it has rolled or slid up the cloth surface (104), then enters the recess (105), subsequently rolls or slides out of the recess (105) again and only then rolls or slides down the cloth surface (104). The invention also relates to the use of this tennis wall as an aid in tennis training.

13 Claims, 4 Drawing Sheets

(56) References Cited

U.S. PATENT DOCUMENTS

| | | | | |
|---|---|---|---|---|
| 2,174,884 | A | * | 10/1939 | Kachel .................... A63B 67/04 473/434 |
| 3,180,643 | A | * | 4/1965 | Kallai .................... A63B 63/00 473/434 |
| 4,239,235 | A | * | 12/1980 | Torres ................ A63B 69/0097 473/434 |
| 4,417,728 | A | * | 11/1983 | Hay ....................... A63B 63/00 273/342 |
| 4,703,931 | A | * | 11/1987 | Steen ................. A63B 69/0097 473/197 |
| 5,306,009 | A | * | 4/1994 | Bolanos ................. A63B 63/00 473/157 |
| 5,672,125 | A | * | 9/1997 | Ross .................... A63B 71/022 473/421 |
| 5,795,252 | A | * | 8/1998 | Crucet ................. A63B 71/022 52/9 |
| 5,938,546 | A | * | 8/1999 | Caruso ............... A63B 69/0097 473/434 |
| 6,082,736 | A | * | 7/2000 | Barlow .................... A63D 3/02 273/317.1 |
| 6,165,085 | A | * | 12/2000 | Lubin .................. A63B 63/004 273/400 |
| 9,155,952 | B2 | | 10/2015 | Yamanashi |
| 2005/0200079 | A1 | * | 9/2005 | Barber ....................... F41J 1/10 273/400 |
| 2010/0022333 | A1 | * | 1/2010 | Gaudin ................. A63B 63/00 473/478 |
| 2012/0283046 | A1 | * | 11/2012 | Yamanashi ........ A63B 69/0097 473/432 |
| 2014/0296002 | A1 | | 10/2014 | Luo |
| 2015/0297969 | A1 | * | 10/2015 | Flis .................... A63B 69/0097 473/435 |
| 2016/0175682 | A1 | * | 6/2016 | Patton ................ A63B 69/0097 473/431 |

FOREIGN PATENT DOCUMENTS

| | | |
|---|---|---|
| DE | 3034332 C1 | 4/1984 |
| EP | 0220111 A2 | 4/1987 |
| GB | 2059179 B | 6/1983 |
| NL | 2005369 C2 | 3/2012 |
| WO | 8001650 A1 | 8/1980 |

OTHER PUBLICATIONS

International Preliminary Report on Patentability; European Patent Office; International Application No. PCT/EP2019/025013; dated Jan. 9, 2020; 19 pages.

First Office Action and Search Report; China National Intellectual Property Administration; CN Application No. 201980009085.0; dated Dec. 30, 2020; 9 pages.

International Search Report; European Patent Office; International Application No. PCT/EP2019/025013; dated Mar. 15, 2019; 5 pages.

* cited by examiner

TENNIS WALL

CROSS-REFERENCE TO RELATED APPLICATIONS

This application is a U.S. National Phase of International PCT Application No. PCT/EP2019/025013 filed Jan. 11, 2019, which claims priority to German Patent Application Serial No. 10 2018 000 367.2 filed Jan. 18, 2018, the contents of each application are incorporated herein by reference in their entirety.

The present invention concerns a tennis wall and the use of a tennis wall as an aid in tennis training.

Tennis is a technically sophisticated sport. In tennis, it is therefore—especially for beginners—very important to learn the fundamental technical skills so that a game with partners, in which rallies occur, can be played as soon as possible.

A flexible tennis wall supports the training process. With the help of the wall, players can carry out many repetitions to train strokes in a short period of time. Through regular repetitions, players become more confident and learn in a short time, for example, the right timing, the perfect hitting spot and a good swing. Existing state of the art tennis walls include a piece of cloth that is stretched diagonally into a frame. After the player has carried out the stroke, the ball hits the cloth. Depending on how tightly the fabric is stretched in the frame, the fabric can absorb part of the impulse of the tennis ball's impact, and then the tennis ball rolls or slides up the surface of the cloth at a constant angle. At the end of the cloth there is a barrier that stops the ball, which then rolls or slides down again. At the bottom of the cloth usually a bouncing device is provided, which serves to guide the ball back towards the player. Such tennis walls are commercially marketed, for example, by the company Tri-tennis® Nederland, s'Hertogen-bosch, the Netherlands.

However, the disadvantage of these existing state of the art tennis walls is that the time intervals between strokes, though they vary somewhat from manufacturer to manufacturer, are often not sufficiently long enough. After only a short while a player is often no longer able to swing back the arm fast enough in order to perform the next stroke correctly, in accordance with the good tennis technique to be learned. Targeted training—especially for beginners and when playing by yourself at the wall—is not realistic at the pace at which conventional tennis walls play the ball back. This is due to the fact that the angle between the cloth and the ground in conventional tennis walls is constant everywhere along the entire running track of the ball and that the dimensions of these tennis training walls are limited both in depth and height. However, in order to extend the time intervals, the length of the fabric's surface on which the ball rolls or slides up, then is stopped and subsequently rolls or slides down, cannot be extended arbitrarily. This is because tennis training walls are used independently of location—also in private home settings—and must therefore also take into account the common space conditions in garages, carports, gardens, terraces or basements.

In practice, the problem with too little time between rallies can be partly avoided by letting the ball bounce additionally onto the ground after the first rebound and then take the next shot. This requires, however, that the ground on which the tennis training wall is placed is very even (for example, a level concrete ground) so that the ball cannot bounce off-track and that there is also enough space to the rear for this second bounce. Furthermore, this solution is only feasible for experienced players. The further away a player stands from the wall, the more precisely he must aim to hit the surface of the tennis wall. Especially beginners should therefore stand as close to the wall as possible in order to hit it ideally.

The object of the present invention was to overcome the disadvantages known in connection with state of the art tennis walls.

In particular, the object of the present invention was to design a tennis wall in which the time interval between two strokes can be extended and can also be variably adjusted without having to change the dimensions of the cloth significantly. Advantageously, the tennis wall should also be characterized in that it is not only inexpensive to produce, but also allows for targeted tennis training, even for beginners, on uneven surfaces and with the smallest possible space requirement.

This task would be solved by a tennis wall, comprising
a frame that can be erected on the ground, and
a cloth stretched in said frame,
wherein the cloth is stretched such that a substantially level cloth surface, preferably a level cloth surface, is formed and that a tennis ball hitting the cloth surface rolls or slides up the cloth surface and then rolls or slides down again,
characterized in that a recess is provided on the upper end of the cloth, the recess being designed and arranged such that a tennis ball, once it has rolled or slid up the cloth surface, then enters the recess, subsequently rolls or slides out of the recess again and not before then rolls or slides down the cloth surface.

Surprisingly, it has been shown that the return speed of a tennis ball on a tennis wall can be easily, reliably and above all, very variably adjusted by providing a recess at the upper end of the cloth into which the ball can enter after rolling up or sliding up the cloth and in which it can remain for a certain, variable retention time. After the player has taken the shot, the ball hits the cloth surface. Upon impact, the cloth can absorb part of the impulse of the tennis ball, depending on how tightly the cloth is stretched in the frame. The tennis ball then rolls or slides upwards at a constant angle along the cloth surface. At the upper end of the cloth, the ball enters into the recess and is stopped there. The ball then rolls or slides out of the recess and then back down the cloth surface. At the bottom, the ball hits a board, or, for example, a small trampoline anchored to or in the frame or standing on the ground, or the ball hits the ground directly. The player is standing in front of the tennis wall and after the ball's impact, the next stroke is carried out. This process is now repeated over and over again in the same rhythm and time interval.

The tennis wall according to the invention includes a frame that can be erected on the ground as one component of the device. The frame of the tennis wall according to the invention can be made of any material that the expert would consider suitable for the construction of a frame of a tennis wall. Preferably the frame is made of metal, for example aluminium, galvanized steel or stainless steel or a combination of these materials, of plastic, for example polyethylene, polypropylene, PET or polycarbonate, or of wood, with the use of an aluminium frame or a frame made of thin-walled galvanized steel or stainless steel being particularly preferred with regard to lightness, stability and corrosion resistance. The frame can also have wheels to make it easier to move the tennis wall from one place to another on the ground.

The tennis wall according to the invention comprises as a further device component a cloth stretched in said frame, the said cloth preferably having a cloth surface bounded by an upper edge, a lower edge, a left side edge and a right side edge. The cloth is stretched in the frame in such a way that a substantially level cloth surface is formed and that a tennis ball hitting the cloth surface can roll up the cloth surface and then roll down again.

The cloth of the tennis wall according to the invention can also be made of any material which the person skilled in the art would consider suitable for such a cloth. Preferably, the cloth is made of plastic, e.g. a truck tarpaulin, an air-permeable, net-like advertising banner ("mesh banner"), e.g. made of PVC, foam or textile-like materials. Weather-resistant materials are particularly preferred, so that the tennis wall can also be operated or used outdoors.

Furthermore, according to the invention, it is preferred that the cloth has a width in a range from 50 to 300 cm, preferably in a range from 80 to 250 cm and even more preferably in a range from 100 to 180 cm and a length (measured up to the beginning of the folding, provided that the recess—as discussed below—is realized by folding the cloth) in a range from 100 to 400 cm, preferably in a range from 150 to 380 cm and even more preferably in a range from 180 to 330 cm. The thickness of the cloth is preferably in a range from 0.1 to 30 mm, and more preferably in a range from 0.5 to 6 mm. If the recess—as discussed below—is realized by folding the cloth, easy foldability should determine the thickness of the cloth.

The cloth can be stretched in the frame using tension springs, rubber bands, expander bands or other, preferably stretchable fastening aids. It must be ensured that the tensioning of the cloth in the frame creates a substantially level cloth surface on which a tennis ball, which hits the cloth at a certain minimum speed, can roll up the cloth surface and then also roll down. By tensioning the cloth in the frame by means of stretchable fastening devices it is ensured, that the cloth can be tensioned in a very user-friendly manner, an level cloth surface is immediately created and the cloth can absorb part of the impulse of the impacting tennis ball.

In accordance with the invention, it is also preferred that the cloth is tensioned in such a way that an angle α in the range from 25 to 70 degrees, particularly preferably in a range of 35 to 55 degrees, is enclosed between the level cloth surface and the ground. The cloth is therefore stretched in the frame (or the frame is constructed in such a way) that the level cloth surface formed by the cloth is inclined obliquely towards the ground in the direction of the player. This tilted position of the cloth ensures that a ball hitting the cloth surface can roll or slide up the cloth surface for a certain distance and then back down again.

The tennis wall according to the invention is now characterized in that a recess is provided on the upper end of the cloth, the recess being designed and arranged such that a tennis ball, once it has rolled or slid up the cloth surface, then enters the recess, subsequently rolls or slides out of the recess again and not before then rolls or slides down the cloth surface. Preferably, a "recess" is understood to be a construction which is provided at the upper end of the cloth surface (or, as discussed in more detail below in connection with a particularly preferred design of the tennis wall according to the invention, which is formed by a folding in the upper area of the cloth) and which comprises an even or slightly curved first surface, preferably directly adjacent to the upper end of the level cloth surface. This first surface includes a reduced angle β between itself and the ground compared to the angle α described above. It is preferable for a tennis ball that has entered into the recess to roll or slide out of the recess along this first level surface (which corresponds to the first part section of the cloth surface described in more detail below), which is less tilted than the larger surface area of the cloth (i.e. compared to the cloth surface which the tennis ball hits first).

According to a particularly preferred embodiment of the tennis wall according to the invention, the recess is formed by a fold in the upper part of the cloth. Preferably, this fold has the shape of a trench which runs essentially in a horizontal direction from the left to the right side of the cloth and preferably extends over the entire width of the cloth.

Figure 2:
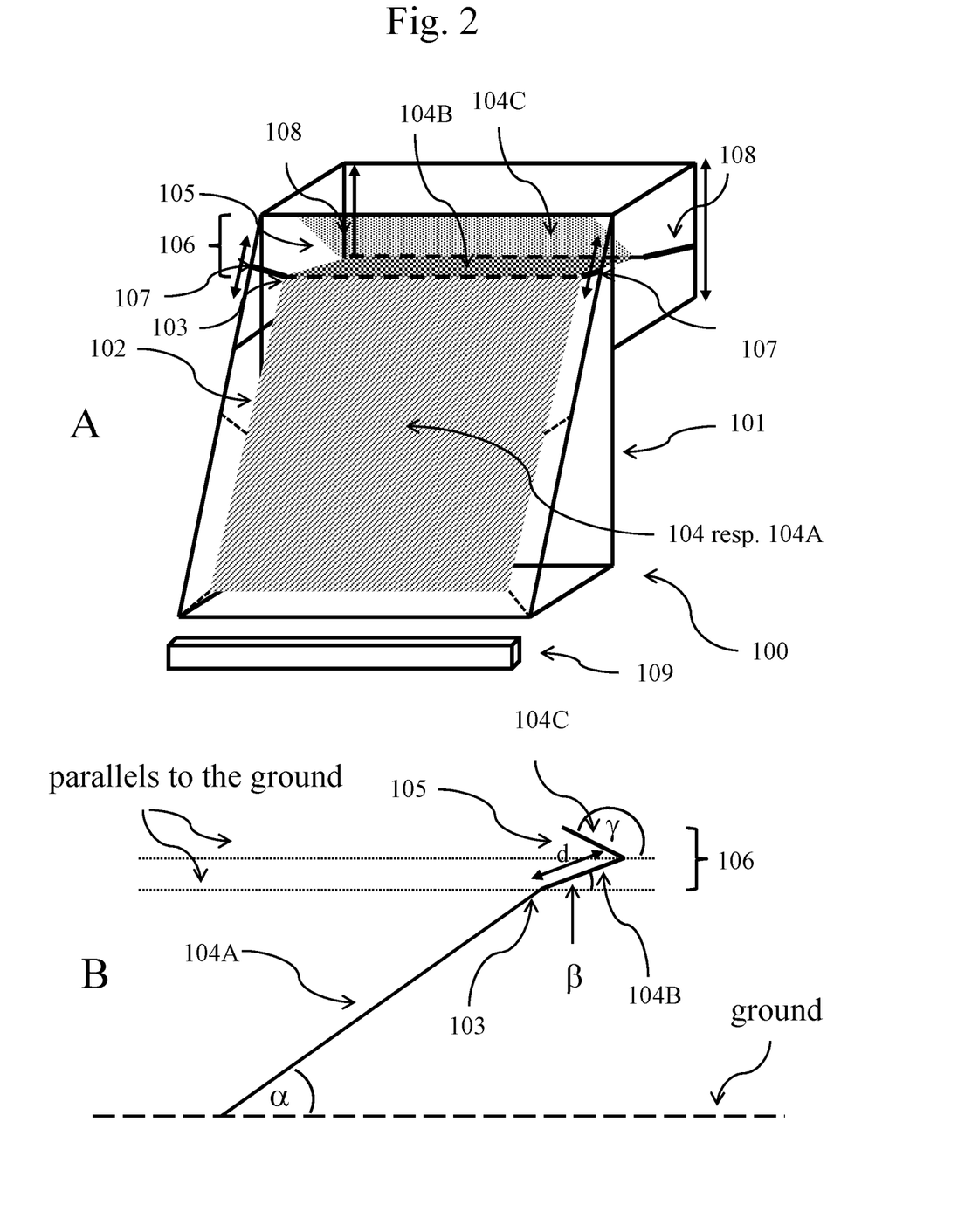

It is particularly preferable in this context that this recess or fold is formed by at least two foldings of the cloth, as exemplified by the two dotted lines in FIG. 2A. The foldings each run in a horizontal direction from the left to the right side of the cloth and extend over the entire width of the cloth. It is still particularly preferred that by means of a first and a second folding a level main cloth surface,
a first level part section of the cloth surface which is adjacent to the level main cloth surface and
a second level part section of the cloth surface, which is adjacent to the first level part section of the cloth surface are formed. The main cloth surface corresponds in its position and orientation to the cloth surface described above, i.e. the cloth surface on which the tennis ball makes contact first when the tennis wall according to the invention is properly used (the upper end of the cloth of the tennis wall according to the invention on which the recess is provided corresponds in this case to the upper end of the level main cloth surface). It is particularly advantageous if the first and the second level part sections of the cloth surface are inclined in such a way that a ball which has rolled up or slid up the main cloth surface and from there has entered the fold will advantageously first hit the second level part section of the cloth surface and, due to the inclination of this level part section of the cloth surface, is directed towards the first level part section of the cloth surface, from where it then rolls or slides out of the fold (see also FIG. 3).

In this context it is particularly preferred that
an angle α is enclosed between the level main cloth surface and the ground;
an angle β is included between the first level part section of the cloth surface and the ground (or rather between the first level part section of the cloth surface and a plane parallel to the ground), which, compared to the angle α, is reduced by at least 5 degrees, preferably by at least 15 degrees and particularly preferably by at least 25 degrees;
an angle γ is included between the second level part section of the cloth surface and the ground (or rather between the second level part section of the cloth surface and a plane arranged parallel to the ground), which, compared to the angle α, is increased by at least 75 degrees, preferably by at least 100 degrees and particularly preferably by at least 120 degrees.

Preferably the angle α is in a range from 25 to 70 degrees, particularly preferably in a range from 35 to 55 degrees, the angle β is in a range from 5 to 30 degrees, particularly preferably in a range of 8 to 20 degrees, and the angle γ is in a range of 130 to 190 degrees, particularly preferably in a range of 150 to 180 degrees.

Figure 4:
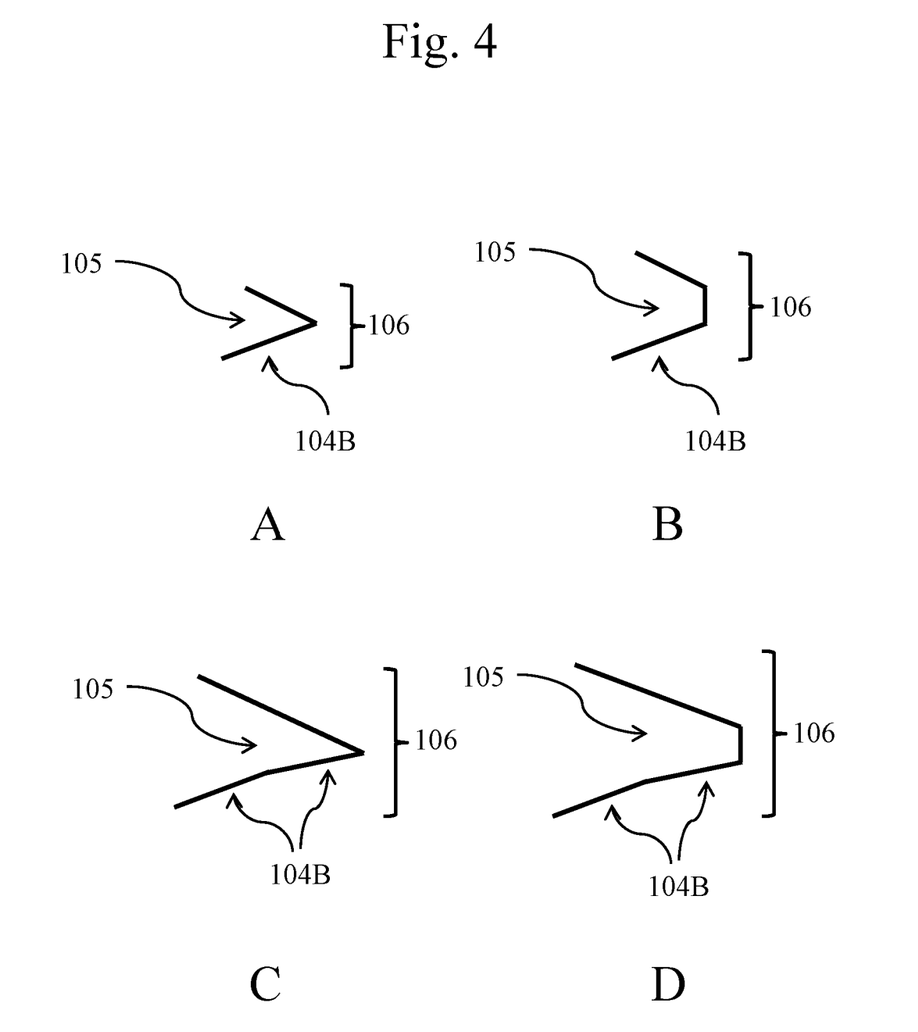
FIGS. 4A to 4D show different profiles of a fold 105 formed by folding the top end 103 of the cloth 102.

The type and number of folding of the cloth to form the recess or fold can be arbitrarily varied. In the simplest case of only two folds as described above, a tapered, wedge-shaped fold in profile is formed. However, three or more folds are also conceivable, so that more complex folding profiles can also be produced (see also FIG. 4). In particular, it is also conceivable to reduce the angle step by step over two or more adjacent part sections of the cloth surface, as shown for example in FIGS. 4C and 4D.

In connection with this particularly preferred embodiment of the tennis wall according to the invention, in which the recess is formed by a fold in the upper part of the cloth, it is furthermore preferred that the cloth is connected to the frame on the left and right side of the upper end of the cloth by means of a first folding fixation and, respectively, a second folding fixation, and whereby, by means of these folding fixations, the first and the second folding of the cloth is made under formation of a fold. In case the fold is formed by more than two foldings, correspondingly more folding fixations are to be provided. All materials or devices which the specialist considers to be suitable can be selected as folding fixations. For example, these can be bars between the frame ends or ropes made of PVC, nylon or steel, or fixing devices such as rubber and expander loops made of rubber or metal tension springs. In this context, it has also proven to be advantageous that the shape of the fold can be adjusted by means of a first and/or second folding fixation attached to the frame and variable in its position. This way, it is possible to vary the angles β and γ and also the length d (see FIG. 2B) along which the tennis ball runs or slides into the fold on the first level part section of the cloth surface formed by the first folding, and thus ultimately the overall retention time of the tennis ball in the fold.

Preferably the retention time (i.e. the time which passes between the ball's entry into the recess and its release from the recess) of a tennis ball in the recess, particularly preferably in the fold formed by the at least two foldings of the cloth, is at least 0.1 seconds, particularly preferably at least 0.5 seconds. In particular, it can be in the range of 0.1 to 3 seconds, preferably in the range from 0.25 to 2 seconds and even more preferably in the range from 0.5 to 1 seconds.

Furthermore, the tennis wall according to the invention may comprise a bouncing device which is arranged in such a way that a tennis ball, after rolling or sliding down the surface of the cloth, falls onto this bouncing device and is guided by it towards the player. Such a bouncing device may be connected to or be part of the frame or be placed on the ground in front of the frame as a separate element of the tennis wall. Examples of suitable rebound devices are simple planks or boards fixed to the frame, or a trampoline or board with a fixed or variable angle located in front of the tennis wall. If there is a change in the alignment of the surface of the bouncing devices, on which the ball bounces after leaving the cloth surface, the angle at which the ball is guided towards the player may be varied.

The present invention also concerns the use of the tennis wall according to the invention as an aid in tennis training, in particular in professional tennis training.

The invention is now explained in more detail by means of non-limiting figures.

FIG. 1A shows a known state of the art tennis wall 100 in a frontal view, while FIG. 1B shows the shape of the cloth 102 in a side view.

FIG. 2A shows a tennis wall 100 according to the invention in a front view, while FIG. 2B shows the shape of the cloth 102 in a side view.

Figure 1:
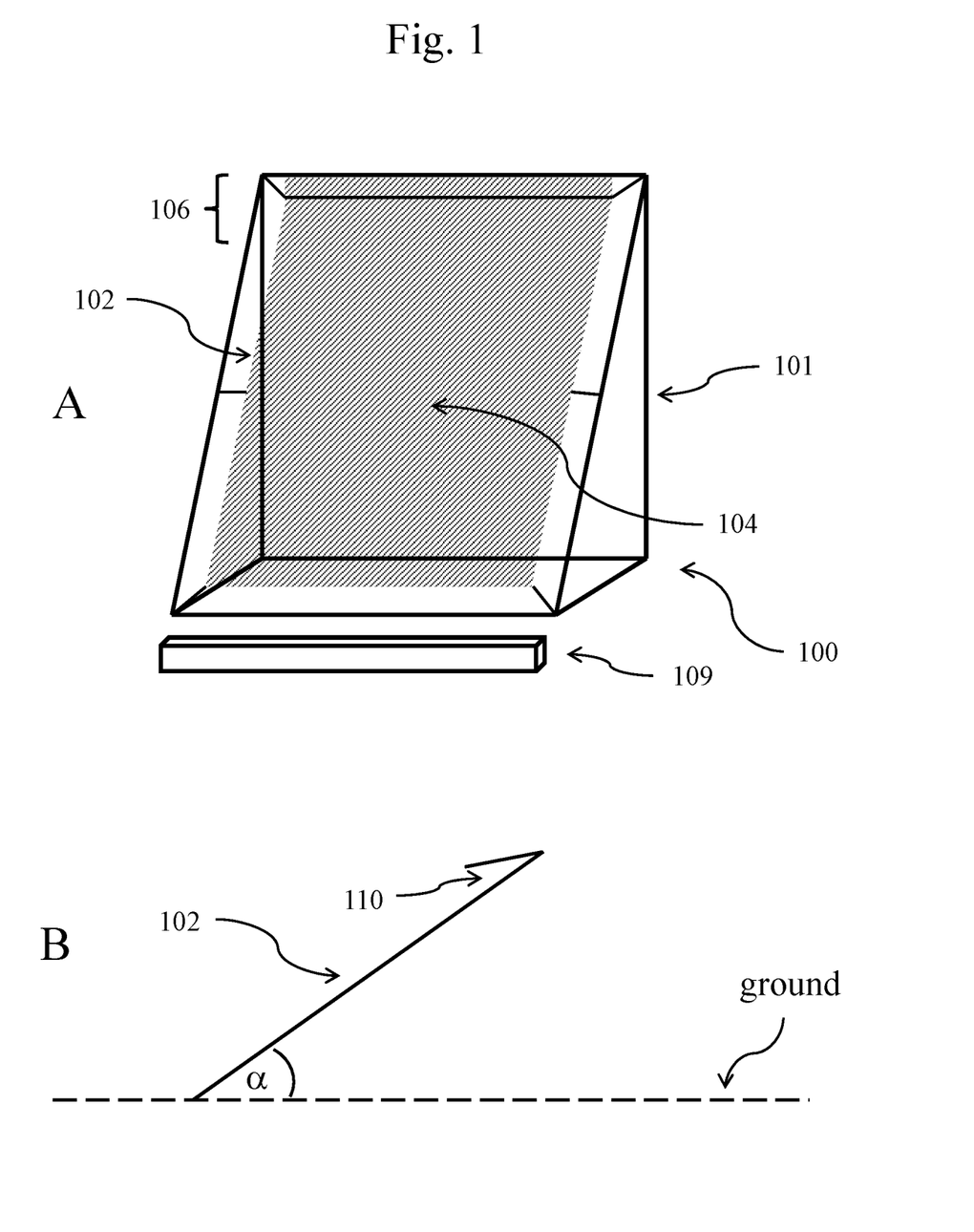

FIG. 1A shows a known state of the art tennis wall 100 in a frontal view, while FIG. 1B shows the shape of the cloth in a side view. Such a conventional tennis wall 100, as commercially marketed by, for example, Tri-tennis® Nederland, s'Hertogenbosch, Netherlands, comprises a frame 101 placed on the ground and a cloth 102 stretched in this frame, the cloth 102 being stretched in the frame in such a way that it forms a substantially level cloth surface 104 tilted towards the ground in the direction of the player. An angle α is enclosed between the cloth surface 104 and the ground, which is usually in a range from 35 to 55 degrees. When a ball (not shown in FIG. 1A) hits the level cloth surface 104, the cloth 102 can absorb part of the impulse of the tennis ball's impact when the ball makes contact with the cloth, depending on how tightly the cloth 102 is stretched in the frame 101. The ball then runs up the cloth surface 104 at a constant angle until it hits the end point 110 in the upper area 106 of the cloth surface—provided it is played at sufficient speed onto the tennis wall 100 or the cloth surface 104, which is formed in a conventional tennis wall by a simple folding of the cloth 102 at the upper end of the fabric 102. There, the ball is stopped and then runs down again at the cloth surface 104. Once it reaches the bottom end of the cloth 102, the ball hits a bouncing device 109, which is, for example, a bar fixed to the frame 101 or an angle board or trampoline positioned in front of the tennis wall 100, and from there bounces back towards the player, who can then perform the next shot.

Figure 3:
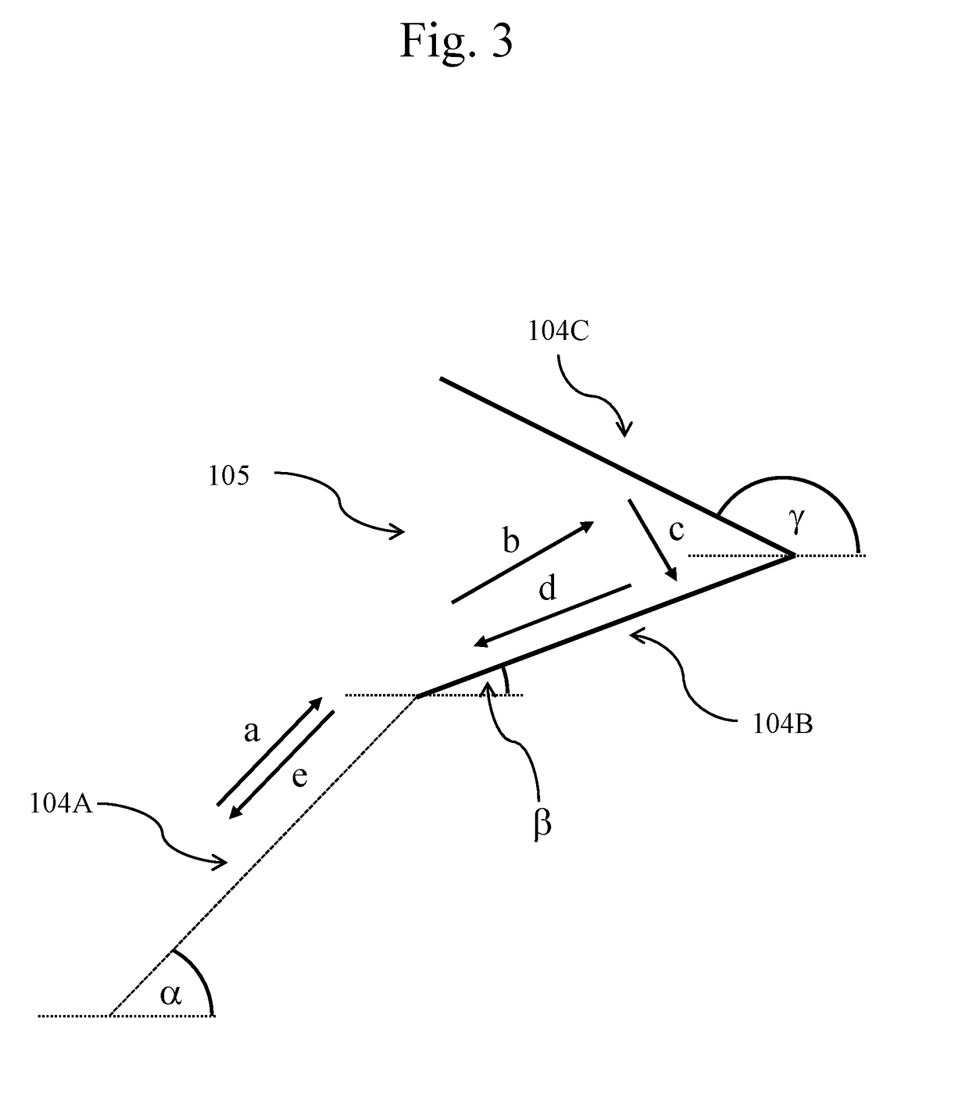
FIG. 3 shows the course of the ball as it enters the recess or fold 105.

FIG. 2A shows a tennis wall 100 according to the invention in a front view, while FIG. 2B shows the shape of the cloth in a side view. In its basic structure, this is comparable to conventional tennis walls. It also comprises a frame 101 placed on the ground and a cloth 102 stretched in this frame, which is stretched in the frame 101 in such a way that it forms a substantially level cloth surface 104 tilted towards the ground in the direction of the player. However, in contrast to a conventional tennis wall, the tennis wall 100 according to the invention has a recess 105 at the upper end 103 of the cloth 102, into which a ball that hits the cloth surface 104 (also not shown in FIG. 2A), enters after it has rolled or slid up the cloth surface 104. In the simplest embodiment shown in FIG. 2A, this recess 105 is formed by a fold 105 in the upper part 106 of the cloth 102, which is realized by two foldings (recognizable by the dotted lines in FIG. 2A). The first and the second folding form a level main cloth surface 104A (which corresponds to the cloth surface 104 in its position and orientation), a first level part section of the cloth surface 104B adjacent to the main cloth surface 104A and second level part section of the cloth surface 104C adjacent to the first level part section of the cloth surface 104B. In this case, the top end 103 of the cloth 102 where the recess 105 is provided, corresponds to the top end of the main cloth surface 104A. In this case, the first and the second level part sections of the cloth surface (104B, 104C) are tilted in such a way that a tennis ball, which has rolled up or slid up the main cloth surface 104A and from there has entered into the fold 105, advantageously first hits the second level part section of the cloth surface 104C and, due to the position of this part section of the cloth surface 104C, is directed towards the first level part section of the cloth surface 104B, from which it then rolls or slides out of the fold 105. This first level part section of the cloth surface 104B has a length d (see FIG. 2B). Compared to the angle α between the main cloth surface 104A and the ground, an angle β is enclosed between the first level part section of the cloth surface 104B and the ground (or between the first level part section of the cloth surface 104B and a plane parallel to the ground), which is reduced compared to angle α (the first level part section of the cloth surface 104B is therefore less tilted than the main cloth surface 104A), while an angle γ is enclosed between the second level part section of the cloth surface 104C and the ground (or between the second level part section of the cloth surface 104C and a plane parallel to the ground) which is increased in comparison with angle α. Also, as can be seen in FIG. 2A, the two foldings are accomplished by means of corresponding folding fixations 107 and 108, by which the left and right sides of the top of the cloth or by which the entire cloth, measured across its width, is or are connected to the frame (the upper left folding fixation 108 is not visible in FIG. 2A, as it is behind the cloth 102). All materials that a person skilled in the art considers suitable can be used for these folding fixations 107 and 108. These can be bars between the frame ends or ropes made of, for example, PVC, nylon or steel, or fixing devices such as rubber and expander slings made of rubber or metal tension springs. As also illustrated by the double arrows in FIG. 2A, the first (lower) folding fixation 107, the second (upper) folding fixation 108 or both folding fixations 107 and 108 can be adjusted in height. In this way, the profile of the fold and thus in particular the angles β and γ as well as the length d and finally the retention time of the ball in the fold 105 can be varied. If a ball hits the level main cloth surface 104A, the cloth 102—depending on how tightly the cloth 102 is stretched in frame 101—can take over part of the impulse of the tennis ball. The ball runs up the main cloth surface 104A until it enters into the recess or fold 105, provided it has been played with sufficient speed onto the tennis wall. As shown in FIG. 3, at this point it can, for example, bounce against the second surface part section of the cloth 104C, from where it is directed back towards the first part section of the cloth surface 104B due to the extent of the inclination of this surface. From this the ball rolls or slides out of the fold 105 and returns to the main cloth surface 104A, where it rolls or slides down. Once it reaches the bottom of the cloth 102, the ball can again hit a conventional rebound device 109 (or even the ground), from where it bounces back towards the player, who can then take the next shot.

FIG. 3 shows an example of a possible course of a tennis ball in tennis wall 100 according to the invention. The ball rolls or slides up the main cloth surface 104A (arrow a). When it reaches the top, it enters into the fold 105 and—if it has been hit hard enough—bounces against the second part section of the cloth surface 104C (arrow b). From there it is carried in the direction of the first part section of the cloth surface 104B (arrow c) (or optionally in the direction of the corner formed in the contact area between the first part section of the cloth surface 104B and the second part section of the cloth surface 104C), on which it then rolls or slides out of the fold 105 (arrow d) and then rolls or slides down the main cloth surface 104A (arrow e). However, it is also conceivable (and not shown in FIG. 3) that the ball after entering the fold 105, if it has been hit less hard, will roll or slide up the first level part section of the cloth surface 104B until it hits the second level part section of the cloth surface 104C and is braked there. It then runs out of fold 105 along the first surface part section of the cloth surface 104B.

FIGS. 4A to 4D show different profiles of a fold 105 formed by folding in the upper surface 106 of the cloth 102. The fold 105 shown in FIG. 4A corresponds to that in FIGS. 2A and 2B. The fold shown in FIG. 4B is formed by triple folding in the upper section 106 of the cloth 102. FIGS. 4C and 4D show configurations of a fold 105 in which the angle α is gradually reduced over two adjacent part sections of the cloth surface 104B.

LIST OF REFERENCE SIGNS 100 tennis wall
101 frame
102 cloth
103 upper end of the cloth 102
104 level cloth surface
104A level main cloth surface
104B first level part section of the cloth surface obtained after the first folding and adjacent to the main cloth surface 104A
104C second level part section of the cloth surface obtained after the second folding and adjacent to first level part section of the cloth surface 104B
105 recess (or fold)
106 upper part of the cloth 102
107 first folding fixation
108 second folding fixation
109 rebounce device
110 end point of a state of the art tennis wall

The invention claimed is:

1. A tennis wall, comprising:
a frame that can be erected on a ground, and
a cloth stretched in said frame,
wherein the cloth is stretched in such a way that a level cloth surface is formed, that an angle α in the range of 25 to 70 degrees is enclosed between the level cloth surface and the ground, and that a tennis ball hitting the cloth surface rolls or slides up the cloth surface and then rolls or slides down again,
wherein a recess is provided at an upper end of the cloth that is formed by a fold in an upper region of the cloth and which has a shape of a trench which runs in a horizontal direction from a left to a right side of the cloth and extends over an entire width of the cloth,
wherein the recess comprises (i) an even first part section of the cloth surface directly adjacent to the upper end of the level cloth surface that includes a reduced angle β between itself and the ground compared to the angle α and (ii) a second level part section of the cloth surface directly adjacent to the even first part section that defines the upper end of the cloth and extends upwardly away from the even first part section at an obtuse angle relative to the ground,
wherein the recess is designed and arranged in such a way that a tennis ball, when it has rolled or slid up the cloth surface and subsequently enters the recess, rolls or slides out of the recess along this first part section of the cloth surface, which is less tilted than the cloth surface, and thereafter rolls or slides down the cloth surface.

2. The tennis wall according to claim 1, wherein the fold is formed by at least two foldings of the cloth.

3. The tennis wall according to claim 2, wherein a first and a second folding are formed to define a level main cloth surface, a first level part section of the cloth surface adjacent to the main cloth surface, and the second level part section of the cloth surface adjacent to the first level part section of the cloth surface, wherein
an angle β is included between the first level part section of the cloth surface and the ground, which, compared to the angle α, is reduced by at least 5 degrees; and
an angle γ is included between the second level part section of the cloth surface and the ground, which, compared to the angle α, is increased by at least 75 degrees.

4. The tennis wall according to claim 3, wherein the angle β is in a range of 5 to 30 degrees and the angle γ is in a range of 130 to 190 degrees.

5. The tennis wall according to claim 3, wherein the cloth is connected to the frame on the left and right side of the upper end of the cloth in each case via a first folding fixation and a second folding fixation, and wherein by means of these folding fixations the first and the second folding of the cloth takes place with the formation of a fold.

6. The tennis wall according to claim 5, wherein the shape of the fold is adjustable by means of a first variably positioned and/or a second variably positioned folding fixation attached to the frame.

7. The tennis wall according to claim 1, wherein a retention time of a tennis ball in the recess is in a range between 0.1 to 3 seconds.

8. Use of a tennis wall according to claim 1 as an aid in tennis training.

9. The tennis wall according to claim 1, wherein the second level part section extends upwardly away from the even first part section at the obtuse angle relative to the ground such that the second level part section overhangs the even first part section.

10. The tennis wall according to claim 9, wherein the second level part section overhangs the even first part section over the entire width of the cloth.

11. The tennis wall according to claim 9, wherein the second level part section defines an uppermost point of the cloth in a vertical direction.

12. The tennis wall according to claim 9, wherein the second level part section defines an uppermost periphery of the trench in a vertical direction.

13. The tennis wall according to claim 9, wherein in use of the tennis wall, the second level part section is configured to direct a tennis ball downward in a vertical direction to cause the tennis ball to contact the even first part section before exiting the recess.

* * * * *